United States Patent [19]
Ishida et al.

[11] 4,392,968
[45] Jul. 12, 1983

[54] METAL DEACTIVATOR AND COMPOSITION CONTAINING SAME

[75] Inventors: Noboru Ishida, Sagamihara; Harumichi Watanabe, Yokohama, both of Japan

[73] Assignee: Nippon Oil Company, Limited, Tokyo, Japan

[21] Appl. No.: 288,343

[22] Filed: Jul. 30, 1981

[30] Foreign Application Priority Data

Aug. 13, 1980 [JP] Japan ................................ 55-110391
Aug. 13, 1980 [JP] Japan ................................ 55-110392

[51] Int. Cl.³ .............................................. C10M 1/32
[52] U.S. Cl. .................................. 252/51.5 R; 252/50; 252/401; 252/403; 546/176; 546/179; 548/254
[58] Field of Search ................ 252/50, 51.5 R, 401, 252/403; 546/176, 179; 548/254

[56] References Cited

U.S. PATENT DOCUMENTS

| | | | |
|---|---|---|---|
| 2,198,961 | 4/1940 | Dietrich | 252/51.5 R X |
| 2,458,526 | 1/1949 | Oberright | 252/51.5 R |
| 2,470,085 | 5/1949 | Harvill et al. | 548/254 |
| 2,647,824 | 8/1953 | Jones et al. | 252/51.5 R X |
| 2,681,910 | 6/1954 | Burckhalter | 546/179 X |
| 3,346,496 | 10/1967 | Neumann et al. | 252/51.5 R X |
| 4,142,029 | 2/1979 | Illy | 548/254 |
| 4,285,823 | 8/1981 | Sung et al. | 252/50 |

FOREIGN PATENT DOCUMENTS

| | | | |
|---|---|---|---|
| 1511819 | 2/1968 | France | 252/50 |
| 41-3703 | 3/1966 | Japan | 546/176 |

*Primary Examiner*—Andrew Metz
*Attorney, Agent, or Firm*—Austin R. Miller

[57] ABSTRACT

The oxidation of a lubricating oil caused by metal components can be suppressed effectively by adding to the lubricating oil a compound represented by the formula

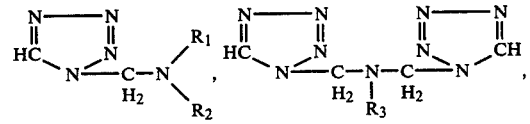

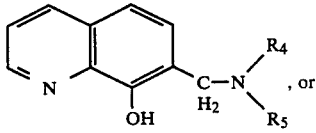

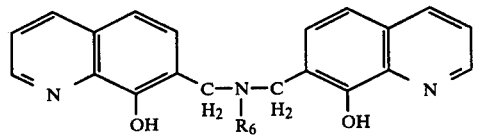

7 Claims, No Drawings

METAL DEACTIVATOR AND COMPOSITION CONTAINING SAME

BACKGROUND OF THE INVENTION

This invention relates to a metal deactivator and a composition containing the same. More particularly, it is concerned with a metal deactivator having a new chemical structure suitable as an additive to lubricating oils or the like and also with a composition containing the same.

The metal deactivator is an additive for deactivating dissolved metal salts which promote the oxidation of fuels and lubricating oils or for forming an inert film on the metal surface. As the metal deactivator there are widely known benzotriazole, its derivatives, and thiadiazole. But these compounds have not always been satisfactory in their performance.

SUMMARY OF THE INVENTION

It is an object of this invention to provide a new metal deactivator having a superior performance to that of conventional metal deactivator.

It is another object of this invention to provide a composition containing a new metal deactivator.

Other objects and advantages of this invention will become apparent from the following description.

The aforesaid objects of this invention can be attained by a metal deactivator comprising at least one member selected from the group consisting of compounds represented by the formula I

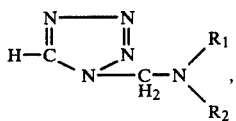

compounds represented by the formula II

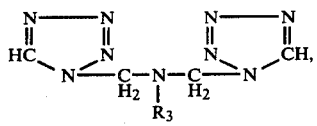

compounds represented by the formula III

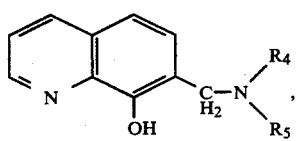

and compounds represented by the formula IV

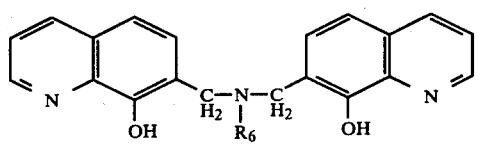

and also by a composition comprising at least one member selected from the group consisting of mineral and synthetic oils having a kinematic viscosity of 10 to 10,000 cSt (40° C.) and a viscosity index of not less than 80, and 0.001% to 10.0% by weight, based on the total weight of the composition, of the above metal deactivator. In the above formulae I, II, III and IV, $R_1$, $R_2$, $R_3$, $R_4$, $R_5$ and $R_6$, which may be alike or different, are each a hydrogen atom, an alkyl group having 1 to 20 carbon atoms, an alkenyl group having 2 to 20 carbon atoms, a cycloalkyl group having 5 to 12 carbon atoms, an aryl group having 6 to 10 carbon atoms, an aralkyl group having 7 to 9 carbon atoms, or a group represented by the formula $R_7O(R_8O)_nR_9$ wherein $R_7$ is a hydrogen or an alkyl group having 1 to 20 carbon atoms, $R_8$ and $R_9$ are each independently an alkylene group having 2 or 3 carbon atoms and n is an integer of 0 to 4.

DETAILED DESCRIPTION OF THE INVENTION

A more detailed description will be given hereinunder about a metal deactivator and a composition containing the same both according to this invention.

The compounds represented by the formulae I and II are tetrazol derivatives, in which formulae $R_1$, $R_2$ and $R_3$ may be alike or different; that is, in the case of using a compound of the formula I, $R_1$ and $R_2$ may be alike or different, and in the case of using a mixture of a compound of the formula I and a compound of the formula II, $R_1$, $R_2$ and $R_3$ may be alike or different.

The compounds represented by the formulae III and IV are hydroxyquinoline derivatives, in which formulae $R_4$, $R_5$ and $R_6$ may be alike or different; that is, in the case of using a compound of the formula III, $R_4$ and $R_5$ may be alike or different, and in the case of using a mixture of a compound of the formula III and a compound of the formula IV, $R_4$, $R_5$ and $R_6$ may be alike or different. Of course, there may be used a mixture of two or more compounds represented by the same formula, and also there may be employed a mixture of a compound(s) represented by the formula I and/or the formula II and a compound(s) represented by the formula III and/or IV.

In case any one or more of $R_1$ through $R_6$ are each an alkyl group, there may be used alkyl groups having 1 to 20 carbon atoms, but particularly preferred are those having 3 to 18 carbon atoms. Preferred examples are butyl, hexyl, octyl, 2-ethyl-hexyl, decyl, dodecyl, hexedecyl and octadecyl.

In case any one or more of $R_1$ through $R_6$ are each an alkenyl group, there may be used alkenyl groups having 2 to 20 carbon atoms, but particularly preferred are those having 3 to 18 carbon atoms. Preferred examples are butenyl, octenyl, decenyl, dodecenyl, tetradecenyl and octadecenyl (oleyl).

In case any one or more of $R_1$ through $R_6$ are each a cycloalkyl group, there may be used cycloalkyl groups having 5 to 12 carbon groups with cyclohexyl being a preferred example.

In case any one or more of $R_1$ through $R_6$ are each an aryl group, there may be used aryl groups having 6 to 10 carbon atoms with phenyl and naphthyl being preferred examples.

In case any one or more of $R_1$ through $R_6$ are each an aralkyl group, there may be used aralkyl groups having 7 to 9 carbon atoms with benzyl being a preferred example.

In case any one or more of $R_1$ through $R_6$ are each a group represented by the formula $R_7O(R_8O)_nR_9$, $R_7$ is a hydrogen atom or an alkyl group having 1 to 20 carbon atoms, more preferably a hydrogen atom or an alkyl group having 1 to 8 carbon atoms and still more preferably a hydrogen atom, $R_8$ and $R_9$ are each an alkylene group having 2 to 3 carbon atoms, and n is an integer of 0 to 4 and more preferably 0. Preferred examples are hydroxyethyl, methoxyethyl, n-butoxyethyl, methoxyethoxyethyl, n-butoxyethoxyethyl and n-octyloxypropyloxy.

There is no special limit to the manufacturing method for the tetrazole derivatives or hydroxyquinoline derivatives in this invention. For example, however, in order to obtain a compound of the formula I, the Mannich reaction of tetrazole, a secondary amine which satisfies the foregoing conditions of $R_1$ and $R_2$ and formaldehyde is preferred, and in order to obtain a compound of the formula II, the Mannich reaction of tetrazole, a primary amine which satisfies the foregoing conditions of $R_3$ and formaldehyde is preferred. Furthermore, in order to obtain a compound of the formula III, the Mannich reaction of 8-hydroxyquinoline, a secondary amine which satisfies the foregoing conditions of $R_4$ and $R_5$ and formaldehyde is preferred, and in order to obtain a compound of the formula IV, the Mannich reaction of 8-hydroxyquinoline, a primary amine which satisfies the foregoing condition of $R_6$ and formaldehyde is preferred.

Among the metal deactivating compounds according to this invention, the compounds represented by the formula I and III are more preferable, and particularly preferred are those wherein $R_1$, $R_2$, $R_4$ and $R_5$ are alike or different and are alkyl groups having 3 to 18 carbon atoms, especially hexyl, octyl, decyl, dodecyl, hexadecyl and octadecyl.

The composition of this invention contains 0.001% to 10.0% by weight, preferably 0.01% to 1.0% by weight, of at least one of the foregoing metal deactivating compounds, and the whole or main part of the balance is a mineral oil and/or a synthetic oil having a kinematic viscosity of 10 to 10,000 cSt (40° C.), preferably 90 to 200. As the mineral oil there is preferably used a lubricating oil fraction of petroleum after refining by hydrotreating, clay treating, solvent refining or a combination thereof. Preferred examples of the synthetic oil are polybutenes, poly-$\alpha$-olefins, diesters, polyol esters, and mixtures thereof. If the amount of the metal deactivator is smaller than 0.001% by weight, it will be impossible for the same agent to display the expected effect, while a larger amount thereof than 10.0% by weight is not desirable from the economic point of view.

In the composition of this invention there may be incorporated, if required in addition to the aforesaid metal deactivator, an anti-oxidant, a detergent-dispersant, a viscosity index improver, a pour-point depressant, a rust preventive agent, an extreme-pressure agent, an oiliness improver, or an antifoaming agent. The details of these additives is disclosed, for example, in the "Lubrication Society Proceedings Vol. 15 No. 6" or Toshio Sakurai, "Petroleum Product Additives" (Saiwai Shobo).

The metal deactivator and the composition containing same of this invention are preferably used as additives to lubricating oils, for example, turbine oil, hydraulic oil, gear oil, gasoline-engine oil, diesel-engine oil, marine-engine oil, compressor oil, oil-film bearing oil, refrigerator oil, slide-way lubricating oil, rolling oil, machine tool oil, automatic transmission oil, various metalworking oils and greases, and also to electrical insulating oil, heat transfer oil and rust preventive oil.

The following are preparation examples, working examples and comparative examples for further illustration of this invention.

PREPARATION EXAMPLE 1

150 ml. of methanol was added to 7.0 g. of tetrazole and 24.1 g. of bis(2-ethylhexyl)amine and stirring was made in a nitrogen gas stream, to which was dropwise added 10.4 ml. of a 35% aqueous formalin solution, and reaction was allowed to proceed for 1 hour at 25° C. followed by refluxing for 5 hours in the presence of methanol. Thereafter, the reaction product was filtered and methanol removed, then n-hexane was added and the n-hexane soluble was recovered to yield 265 g. of [bis(2-ethylhexyl)aminomethylene]-1,2,3,4-tetrazole (a compound of the formula I wherein both $R_1$ and $R_2$ are 2ethylhexyl). In the same manner, by the Mannich reaction there were prepared tetrazole derivatives 1 through 12 represented by the formula I and tetrazole derivatives 13 through 15 represented by the formula II.

TABLE 1

Preparation of tetrazole derivatives represented by the formula I

| Compound | $R_1$ | $R_2$ | Analysis | | |
|---|---|---|---|---|---|
| | | | % C | % H | % N |
| (I)-1 | 2-ethylhexyl | 2-ethylhexyl | 67.1 | 11.4 | 21.5 |
| (I)-2 | n-butyl | n-butyl | 56.7 | 10.3 | 33.8 |
| (I)-3 | n-hexyl | n-hexyl | 62.9 | 10.8 | 26.2 |
| (I)-4 | n-octyl | n-octyl | 66.9 | 11.4 | 21.7 |
| (I)-5 | cyclohexyl | cyclohexyl | 63.4 | 10.1 | 26.4 |
| (I)-6 | n-octadecyl | n-octadecyl | 75.6 | 12.7 | 11.6 |
| (I)-7 | nonenyl | nonenyl | 69.1 | 10.6 | 20.1 |
| (I)-8 | phenyl | phenyl | 66.9 | 5.2 | 27.9 |
| (I)-9 | octylphenyl | octylphenyl | 76.1 | 9.9 | 13.8 |
| (I)-10 | n-octyloxy propyloxy | n-octyloxy propyloxy | 60.8 | 10.7 | 14.8 |
| (I)-11 | benzyl | benzyl | 68.9 | 6.1 | 25.0 |
| (I)-12 | phenyl | n-octyl | 76.7 | 8.7 | 14.5 |

TABLE 2

Preparation of tetrazole derivatives represented by the formula II

| Compound | $R_3$ | Analysis | | |
|---|---|---|---|---|
| | | % C | % H | % N |
| (II)-13 | nonylphenyl | 58.5 | 7.8 | 32.8 |
| (II)-14 | octadecyl | 60.9 | 9.9 | 29.1 |
| (II)-15 | cyclohexyl | 45.4 | 6.8 | 47.7 |

EXAMPLES 1–15 AND COMPARATIVE EXAMPLES 1, 2

The tetrazole derivatives 1 through 15 obtained in Preparation Example 1 were added to a mineral oil and their performance as a metal deactivator was evaluated according to the following copper plate corrosion test and oxidation test, the results of which are shown in Table 3.

In the copper plate corrosion test, first a sample oil was prepared by adding 1.0 wt.% of olefin sulfide (sulfur concentration 40.8%) to "FBK Turbine Oil 32" (a product of Nippon Oil Co.) (kinematic viscosity 32.5 cSt at 40° C., viscosity index 102), then 0.01 wt.% of the tetrazole derivatives was added to the sample oil, and there was conducted a copper plate corrosion test (at 100° C., 3 hours) according to JIS K 2513 which corresponds to ASTM-D 130.

In the oxidation text, 0.1 wt.% of the tetrazole derivatives was added to the "FBK Turbine Oil 32" (a product of Nippon Oil Co.) and there was made a rotary pump oxidation test (at 150° C., oxygen pressure 13 kg/cm², using a copper wire catalyst) according to ASTM D 2272, then the results were evaluated in terms of time required to absorb 1.8 kg/cm² of oxygen.

TABLE 3

| | | Test Results | |
|---|---|---|---|
| | Metal deactivator | Copper Plate Corrosion Test | Oxidation Test (minutes) |
| Example 1 | Tetrazole derivative (I)-1 | 1a | 850 |
| 2 | (I)-2 | 1a | 841 |
| 3 | (I)-3 | 1a | 868 |
| 4 | (I)-4 | 1a | 828 |
| 5 | (I)-5 | 1a | 761 |
| 6 | (I)-6 | 1a | 428 |
| 7 | (I)-7 | 1a | 380 |
| 8 | (I)-8 | 1a | 675 |
| 9 | (I)-9 | 1a | 451 |
| 10 | (I)-10 | 1a | 365 |
| 11 | (I)-11 | 1a | 784 |
| 12 | (I)-12 | 1a | 841 |
| 13 | (I)-13 | 1a | 673 |
| 14 | (I)-14 | 1a | 748 |
| 15 | (I)-15 | 1a | 646 |
| 16 | (I)-1 + (II)-13 (50 wt % + 50 wt %) | 1a | 780 |
| Comparative | | | |
| Example 1 | None | 2a | 234 |
| 2 | Benzotriazole | 1a | 311 |

The tetrazole derivatives according to this invention exhibited a superior performance in both copper plate corrosion test and oxidation test, and also in their application as lubricating oils such as turbine oil and hydraulic oil they showed a desirable performance.

PREPARATION EXAMPLE 2

150 ml. of methanol was added to 16.0 g. of 8-hydroxyquinoline and 24.2 g. of bis(2-ethylhexyl)amine and stirring was made at 20° C., to which was dropwise added 10.4 ml. of a 35% aqueous formalin solution, and reaction was allowed to proceed for 1 hour at 20° C. followed by refluxing for 3 hours at the boiling point of methanol. The reaction product, after adding water and methanol, was extracted with n-hexane, the solvent was removed and subsequent drying yield 22.5 g. of 7-bis(2-ethylhexyl)aminomethylene-8-hydroxyquinoline (a compound of the formula III wherein both $R_1$ and $R_2$ are 2-ethylhexyl). In the same manner, by the Mannich reaction there were prepared hydroxyquinoline derivatives 1 through 13 represented by the formula III and hydroxyquinoline derivatives 14 through 17 represented by the formula IV.

TABLE 4

Preparation of hydroxyquinoline derivatives represented by the formula III

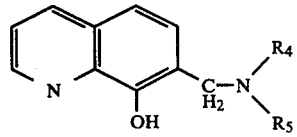

| | | | Analysis | | | |
|---|---|---|---|---|---|---|
| Compound | $R_4$ | $R_5$ | % C | % H | % N | O |
| (III)-1 | 2-ethylhexyl | 2-ethylhexyl | 78.1 | 10.9 | 7.0 | 4.0 |
| (III)-2 | n-butyl | n-butyl | 75.6 | 9.2 | 9.6 | 5.5 |
| (III)-3 | n-hexyl | n-hexyl | 77.3 | 10.1 | 8.0 | 4.6 |
| (III)-4 | n-octyl | n-octyl | 78.0 | 11.0 | 7.0 | 4.0 |
| (III)-5 | n-dodecyl | n-dodecyl | 79.6 | 11.8 | 5.5 | 3.0 |
| (III)-6 | cyclohexyl | cyclohexyl | 77.1 | 9.9 | 8.2 | 4.7 |
| (III)-7 | n-octadecyl | n-octadecyl | 81.1 | 12.3 | 4.1 | 2.3 |
| (III)-8 | iso-dodecenyl | iso-dodecenyl | 78.2 | 11.7 | 5.5 | 3.0 |
| (III)-9 | phenyl | phenyl | 79.8 | 6.7 | 8.5 | 4.8 |
| (III)-10 | octylphenyl | octylphenyl | 81.9 | 10.1 | 5.1 | 2.8 |
| (III)-11 | n-octyloxy propyloxy | n-octyloxy propyloxy | 73.8 | 11.5 | 5.3 | 9.2 |
| (III)-12 | benzyl | benzyl | 80.4 | 7.2 | 7.8 | 4.4 |
| (III)-13 | phenyl | n-octyl | 78.9 | 9.0 | 7.6 | 4.3 |

TABLE 5

Preparation of hydroxyquinoline derivatives represented by the formula IV

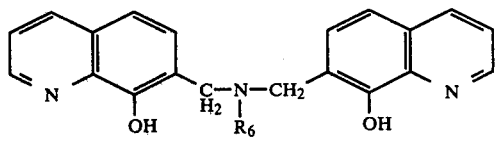

| | | Analysis | | | |
|---|---|---|---|---|---|
| Compound | $R_6$ | % C | % H | % N | % O |
| (IV)-14 | nonylphenyl | 78.0 | 8.2 | 7.8 | 5.9 |
| (IV)-15 | 2-ethylhexyl | 75.1 | 8.2 | 9.4 | 7.1 |
| (IV)-16 | octadecyl | 77.6 | 9.7 | 7.2 | 5.4 |
| (IV)-17 | cyclohexyl | 74.6 | 7.6 | 10.0 | 7.6 |

EXAMPLES 17-34 AND COMPARATIVE EXAMPLES 3, 4

The hydroxyquinoline derivatives 1 through 17 obtained in Preparation Example 2 were added to a mineral oil and their performance as a metal inactivating agent was evaluated according to the foregoing copper plate corrosion test and oxidation test, the results of which are shown in Table 6.

TABLE 6

| | | Test Results | |
|---|---|---|---|
| | Metal deactivator | Copper Plate Corrosion Test | Oxidation Test (minutes) |
| Example 17 | Hydroxyquinoline derivative (III)-1 | 1a | 717 |
| 18 | (III)-2 | 1a | 601 |
| 19 | (III)-3 | 1a | 590 |
| 20 | (III)-4 | 1a | 589 |
| 21 | (III)-5 | 1a | 501 |
| 22 | (III)-6 | 1a | 318 |
| 23 | (III)-7 | 1a | 323 |
| 24 | (III)-8 | 1a | 344 |
| 25 | (III)-9 | 1a | 381 |
| 26 | (III)-10 | 1a | 329 |

TABLE 6-continued

| Metal deactivator | | Copper Plate Corrosion Test | Oxidation Test (minutes) |
|---|---|---|---|
| 27 | (III)-11 | 1b | 319 |
| 28 | (III)-12 | 1a | 479 |
| 29 | (III)-13 | 1a | 401 |
| 30 | (IV)-14 | 1a | 511 |
| 31 | (IV)-15 | 1a | 526 |
| 32 | (IV)-16 | 1a | 491 |
| 33 | (IV)-17 | 1a | 523 |
| 34 | (III)-1 + (IV)-14 (50 wt % + 50 wt %) | 1a | 585 |
| Comparative Example 3 | None | 2a | 234 |

The hydroxyquinoline derivatives according to this invention exhibited a superior performance in both copper plate corrosion test and oxidation test, and also in their application as lubricating oils such as turbine oil and hydraulic oil they showed a desirable performance.

What is claimed is:

1. A metal deactivator comprising at least one member selected from the group consisting of compounds represented by the formula

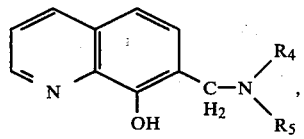

I and compounds represented by the formula

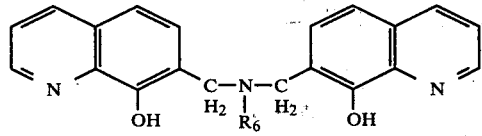

II wherein $R_4$, $R_5$ and $R_6$ are each independently a hydrogen atom, an alkyl group having 1 to 20 carbon atoms, an alkenyl group having 2 to 20 carbon atoms, a cycloalkyl group having 5 to 12 carbon atoms, an aryl group having 6 to 10 carbon atoms, an aralkyl group having 7 to 9 carbon atoms, or a group represented by the formula $R_7O(R_8O)_nR_9$ where $R_7$ is a hydrogen atom or an alkyl group having 1 to 20 carbon atoms, $R_8$ and $R_9$ are each an alkylene group having 2 or 3 carbon atoms and n is an integer of 0 to 4.

2. The metal deactivator as defined in claim 1, in which said member is a compound represented by the formula I.

3. The metal deactivator as defined in claim 1, in which said member is a compound represented by the formula II.

4. The metal deactivator as defined in claim 2, in which $R_4$ and $R_5$ are each independently an alkyl group having 3 to 18 carbon atoms, an alkenyl group having 3 to 18 carbon atoms, cyclohexyl, phenyl, naphthyl, benzyl, or a group represented by the formula $R_7OR_9$ where $R_7$ is a hydrogen atom or an alkyl group having 1 to 8 carbon atoms and $R_9$ is an alkylene having 2 or 3 carbon atoms.

5. A composition comprising an oil selected from the group consisting of mineral oils and synthetic oils, said mineral oils and synthetic oils having a kinematic viscosity ranging from 10 to 10,000 cSt (40° C.) and a viscosity index ranging from 80 to 250, and 0.001% to 10.0% by weight, based on the total weight of the composition, of at least one member selected from the group consisting of compounds represented by the formula

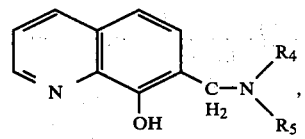

I and compounds represented by the formula

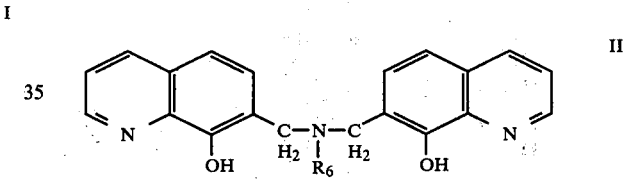

II wherein $R_4$, $R_5$ and $R_6$ are each independently a hydrogen atom, an alkyl group having 1 to 20 carbon atoms, an alkenyl group having 2 to 20 carbon atoms, a cycloalkyl group having 5 to 12 carbon atoms, an aryl group having 6 to 10 carbon atoms, an aralkyl group having 7 to 9 carbon atoms, or a group represented by the formula $R_7O(R_8O)_nR_9$ where $R_7$ is a hydrogen atom or an alkyl group having 1 to 20 carbon atoms, $R_8$ and $R_9$ are each an alkylene group having 2 or 3 carbon atoms and n is an integer of 0 to 4.

6. The composition as defined in claim 5, in which said oil is a mineral or synthetic oil having a kinematic viscosity ranging from 20 to 1,000 cSt (40° C.) and a viscosity index ranging from 90 to 200.

7. The composition as defined in claim 5, in which the content of said member is in the range of from 0.01% to 1.0% by weight.

* * * * *

UNITED STATES PATENT AND TRADEMARK OFFICE
CERTIFICATE OF CORRECTION

PATENT NO. : 4,392,968
DATED : 7/12/83
INVENTOR(S) : Noboru Ishida and Harumichi Watanabe It is certified that error appears in the above-identified patent and that said Letters Patent is hereby corrected as shown below:

Column 1, line 32, delete "H-C" and insert --HC--.

Column 3, line 28, delete "formula" and insert --formulae--.

Column 4, line 17, delete "2ethylhexyl" and insert --2-ethylhexyl--.

Column 6, line 12, before "O" insert --%--.

Signed and Sealed this

Fourth Day of December 1984

[SEAL]

Attest:

GERALD J. MOSSINGHOFF

Attesting Officer     Commissioner of Patents and Trademarks